(12) United States Patent
Cooper et al.

(10) Patent No.: US 9,312,811 B2
(45) Date of Patent: Apr. 12, 2016

(54) BI-STABLE OSCILLATOR

(75) Inventors: Matthew Cooper, Chapel Hill (AU); Alexander Sleptsov, Cambridge (GB); Richard John Hammond, Cambridge (GB)

(73) Assignee: Alere Switzerland GmbH, Zug (CH)

( * ) Notice: Subject to any disclaimer, the term of this patent is extended or adjusted under 35 U.S.C. 154(b) by 918 days.

(21) Appl. No.: 13/574,135

(22) PCT Filed: Jan. 19, 2011

(86) PCT No.: PCT/GB2011/050048
§ 371 (c)(1),
(2), (4) Date: Oct. 17, 2012

(87) PCT Pub. No.: WO2011/089412
PCT Pub. Date: Jul. 28, 2011

(65) Prior Publication Data
US 2013/0029350 A1 Jan. 31, 2013

(30) Foreign Application Priority Data
Jan. 22, 2010 (GB) .................................. 1001129.4

(51) Int. Cl.
*G01N 33/551* (2006.01)
*H03B 5/32* (2006.01)
*G01N 29/02* (2006.01)

(52) U.S. Cl.
CPC ................ *H03B 5/32* (2013.01); *G01N 29/022* (2013.01); *G01N 2291/02466* (2013.01)

(58) Field of Classification Search
None
See application file for complete search history.

(56) References Cited

U.S. PATENT DOCUMENTS

| 2,808,513 A | 10/1957 | Maynard et al. |
| 5,859,572 A * | 1/1999 | Hill .................................. 331/56 |
| 2004/0113707 A1* | 6/2004 | Fredriksson .................. 331/135 |
| 2007/0089513 A1 | 4/2007 | Rosenau et al. |

FOREIGN PATENT DOCUMENTS

WO    WO-9306572 A1    4/1993

OTHER PUBLICATIONS

International Search Report for PCT/GB2011/050048 mailed Mar. 30, 2011.

* cited by examiner

*Primary Examiner* — Chris L Chin
(74) *Attorney, Agent, or Firm* — Foley Hoag LLP (57) ABSTRACT

In accordance with the present invention there is provided a bi-stable oscillator circuit for detecting a load imparted to a surface. The bi-stable oscillator comprises an electrical amplifier, at least one resonator comprising an electrical transducer having a resonant frequency, a surface of the resonator forming the surface on which the load is to be detected and an impedance network having a resonant frequency. The resonator is arranged to be exposed to an environment under test, and the resonator and the impedance network are connected in parallel with the electrical amplifier such that when a load imparted to the surface exceeds a pre-determined threshold value the oscillator circuit oscillates at the resonant frequency of the impedance network and when a load imparted to the surface is less than the threshold value the oscillator circuit oscillates at the resonant frequency of the resonator, switching of the circuit oscillation frequency being indicative of the load crossing the predetermined threshold value.

39 Claims, 7 Drawing Sheets

BI-STABLE OSCILLATOR

STATEMENT REGARDING FEDERALLY SPONSORED RESEARCH AND DEVELOPMENT

This invention was made with US Government support under Grant No. 5U01AI061234-05 awarded by USAMRIID and NIAID. The US Government has certain rights in the invention This application is a 371 national stage application of PCT/GB2011/050048, filed Jan. 19, 2011, which claims priority to GB 1001129.4, filed Jan. 22, 2010. The entire contents of each of these applications are hereby incorporated by reference.

This invention relates to a bi-stable oscillator circuit for detecting any event that imparts a load to a sensor surface and in particular, but not exclusively, a bi-stable oscillator circuit for detecting a biological, chemical or biochemical event.

The use of acoustic transducers is well known in the field of bio-sensors and these have been successfully employed in detection circuits for detecting a broad range of biological and chemical interactions and phenomena. Acoustic transducers are, in general based on quartz crystal resonators such as those found in electronic devices such as watches, computers and televisions. Their utility in bio-sensing is a result of there being a linear relationship between mass adsorbed to the surface of the resonator and the resonant frequency of the crystal. Further, it has subsequently been shown that there is a well defined relationship between and resonant frequency and changes in the viscosity and density of a liquid in which a resonator is immersed.

Such crystal resonators are typically utilised in oscillator circuits in which an alternating electrical signal is applied to the resonator. By applying positive feedback the resonator can be made to oscillate at a resonant frequency. When used as a bio-sensor, typically part of the resonator is coated with material which is capable of binding with a target bio-molecule or cell. When such a receptor is exposed to the target ("ligand") compound, the ligand binds to the substrate causing a change in mass of the sensor (resonator), and/or viscosity or density changes in the local microenvironment of the resonator. Any of these changes will cause a corresponding change in the resonant frequency of the resonator. This in turn will cause a change in the oscillation frequency of the circuit which can be measured by external circuitry or other frequency detection means. Such a combination of a quartz crystal and an oscillator circuit coupled to the quartz crystal to produce an output at a resonant frequency of the crystal is known as a quartz crystal microbalance (QCM).

However, the resonant frequency shift associated with a particular event such as adsorption of material at the resonator surface may be relatively small. For example, the quantity of material adsorbed at the surface in conventional bio-sensing applications is relatively small and thus any corresponding change in resonant frequency will also be small. The detection circuitry involved, therefore, is required to have a high sensitivity. A typical technique for frequency detection would be to utilise a frequency counter circuit connected to the output of the oscillator circuit.

Alternatively a network analyser can be used to analyse the frequency response of the resonator when exposed to a test environment. Another possibility is to use an impulse excitation circuit to determine changes in the impulse response of the resonator circuit caused by an event. These techniques are described in more detail in, for example, "Piezoelectric Sensors", Springer Verlag, Eds. Steinem C., Janshoff A., Springer Series on Chemical Sensors and Biosensors, Vol. 5, 2007, XII, 483 p. 200 illus., ISBN: 978-3-540-36567-9. However, all of the above described techniques require circuits and equipment which are relatively expensive, bulky and complex.

One desirable application of such bio-sensors would be in providing a hand held or portable reader for performing personal testing in the home or elsewhere. Examples of test applications include pregnancy testing, blood coagulation testing or determination of the hematocrit in a blood sample. Known techniques are inherently unsuitable for this type of application because of the bulk and complexity of the detection circuitry required.

It is, therefore, desirable to have an improved sensor (oscillator) circuit in which the circuit is simple and compact while still being capable of effective detection of biological or chemical related events.

In accordance with the present invention there is provided a bi-stable oscillator circuit for detecting a load imparted to a surface comprising an electrical amplifier; at least one resonator comprising an electrical transducer having a resonant frequency, a surface of the resonator forming the surface on which the load is to be detected; an impedance network having a resonant frequency; wherein the resonator is arranged to be exposed to an environment under test, and the resonator and the impedance network are connected in parallel with the electrical amplifier such that when a load imparted to the surface exceeds a pre-determined threshold value the oscillator circuit oscillates at the resonant frequency of the impedance network and when a load imparted to the surface is less than the threshold value the oscillator circuit oscillates at the resonant frequency of the resonator, switching of the circuit oscillation frequency being indicative of the load crossing the predetermined threshold value.

Thus, a bi-stable oscillator circuit is provided which can be used to detect changes in the environment of the resonator which impart a load to the resonator surface. The circuit switches from oscillating at the resonant frequency of the resonator to the resonant frequency of the impedance network when the load imparted to the surface exceeds a threshold. As the circuit can be configured such that the difference between the resonant frequencies is large, the circuit does not require bulky or complex frequency detection circuitry to detect the change in frequency. In a preferred embodiment an offset load is connected with the resonator to configure the switching point of the circuit. Thus, the circuit can by tailored to detect a wide variety of events by careful selection of the impedance value of the offset load. In further embodiments, the circuit can comprise a plurality of resonators or offset loads which can be switched in and out of the circuit (preferably in a pre-determined sequence) to detect difference events or different quantities of change for a particular type of event.

Because the circuit will be preconfigured to correspond to a desired detection event, the instrumentation used to interrogate the circuit(s) is simpler to manufacture compared with a device intended to determine the "resonant frequency status" of a sensor under multiple loading conditions. Accordingly it is possible to utilise the above described circuits in a "hand held reader" instrument that can be used to monitor sensor response to determine information in, for example, the above described applications. Such a system effectively provides a binary, on or off, response, indicating that a predefined condition has been satisfied.

In accordance with a further aspect of the present invention there is also provided a method of detecting a load imparted to a surface utilising a bi-stable oscillator circuit comprising introducing the resonator to an environment to be monitored; detecting the frequency of oscillation of the oscillator circuit after the resonator is introduced to the environment; and determining that the pre-determined load has been imparted to the surface if the frequency of oscillation of the oscillator circuit is substantially equal to the resonant frequency of the impedance network and determining that the pre-determined load has not been imparted to the surface if the frequency of oscillation is substantially equal to the resonant frequency of the resonator.

Embodiments of the present invention will now be described and contrasted with the prior art with reference to the accompanying drawings in which:

FIG. 4b shoes an equivalent circuit diagram of the piezoelectric crystal when connected in series with the offset resistance of FIG. 4a;

Figure 1A:
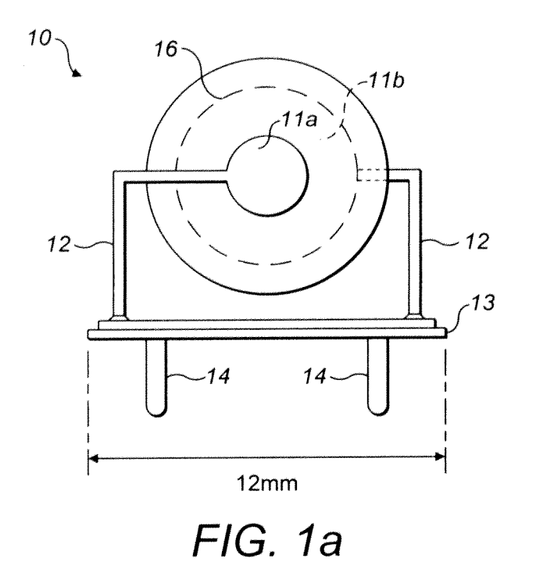
FIG. 1 shows a typical quartz crystal sensor for a microbalance.

A typical quartz sensor for use in a quartz crystal microbalance (QCM) is shown in FIG. 1a. The crystal is a thin slice of quartz from an artificially grown crystal although, as will be appreciated, other piezo-electric materials such as tourmaline, ethylene diamine tartrate, ADP, KDP and Rochelle salt could also be used. Quartz has the advantages of being chemically un-reactive and insoluble in water, as well as being relatively temperature insensitive. The quartz crystal 10 is typically a circular "AT-cut" with metal electrodes 11a and 11b on opposing faces. The electrodes are typically sputtered thin (200 nm) films of gold, silver or titanium, possibly with a sub layer for improved adhesion. Lead wires 12 attach to the electrodes and also provide mechanical support for the crystal as well as some degree of isolation from base 13 of the sensor 10 and lead out wires 12. The crystal is typically around 1 cm in diameter. The change in resonant frequency )F of an AT-cut quartz crystal of area A, vibrating in air at fundamental frequency F, when the mass of the crystal is changed by )M is given approximately by:

$$)F = -2.3 \times 10^6 F^2 )M/A.$$

When used in a QCM the crystal is most frequently used to measure or detect changes in mass at the transducer/sensor surface but it can also be used to detect changes in the viscosity and/or density of a liquid, since when the crystal vibrates in a liquid all these factors effect the resonant frequency of the crystal. The change in resonant frequency of the crystal when a physical load is imparted to the surface of the sensor can be considered in terms of an equivalent circuit as shown in FIG. 1b.

Figure 1B:
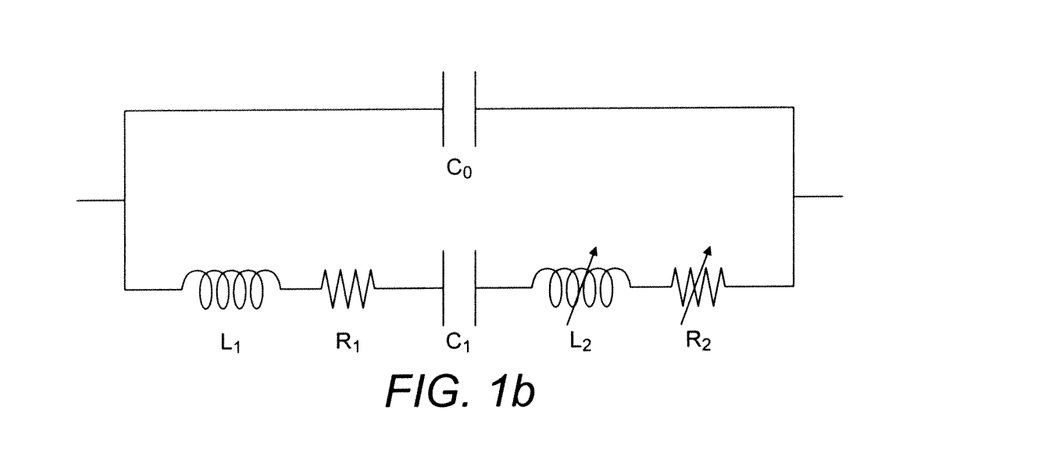
FIG. 1b shows an equivalent circuit of a quartz crystal resonator.

FIG. 1b shows an equivalent circuit corresponding to the crystal. $C_0$ is the crystal's equivalent series capacitance and $L_1$, $R_1$ and $C_1$ the equivalent dry inductance, resistance and capacitance respectively. Equivalent circuit components $L_2$ and $R_2$ are a variable inductance and resistance corresponding to the change in impedance caused when material binds to the crystal surface or when there is a change in environment such as the viscosity and/or density of a liquid to which the resonator is exposed. Thus, the change in environment and/or material binding to the surface imparts a physical load to the surface which causes a change in the electrical properties of the resonator.

The shift in resonant frequency )F of a quartz crystal when immersed in a liquid is given by:

$$)F = -F_0^{3/2} (\eta_L \rho_L / \pi \mu_Q \rho_Q)^{1/2}$$

Where:
)F=Change in Frequency
$F_0$=Resonance frequency
$\eta_L \rho_L$=Liquid absolute density and viscosity
$\mu_Q \rho_Q$=Quartz elastic modulus and density Typically part of one or both electrodes 11a and 11b are coated with material which is capable of binding with a target bio-molecule or cell. When such a receptor is exposed to the target ("ligand") compound, the ligand is bound to the substrate causing a change in mass )M of the sensor, and/or viscosity/density changes in the local microenvironment around the sensor which results in a detectable shift in the resonant frequency of the crystal.

Figure 2:
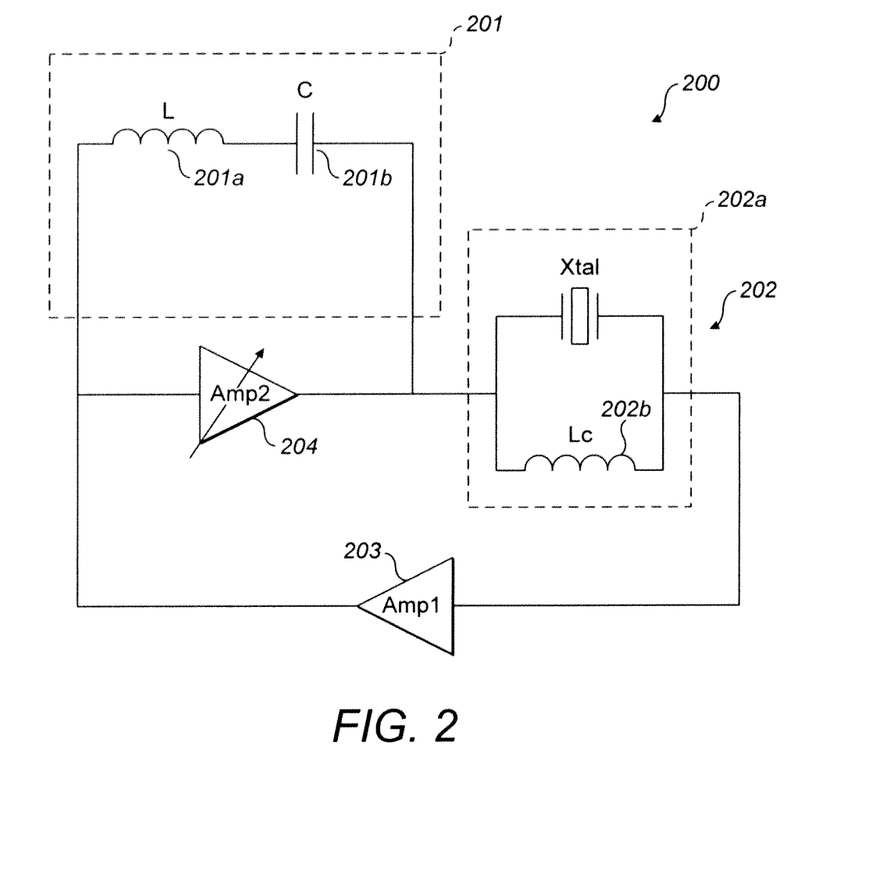
FIG. 2 shows an oscillator circuit in a first embodiment of the present invention.

Turning now to FIG. 2, a circuit diagram is shown of an oscillator circuit incorporating the crystal of FIG. 1 to form a bi-stable oscillator circuit.

As shown, the bi-stable oscillator circuit comprises a piezo-electric quartz crystal Xtal which acts as the resonator in the circuit. In this embodiment, the crystal 202a is connected in parallel to a compensation inductance $L_c$ (202b) which performs a primary role of compensating for the phase shift resulting from the parasitic capacitance inherent in the crystal 202a. The parallel combination of Xtal and $L_c$ form a resonator crystal network 202 which is connected to the input of a first 'buffer' amplifier 203 which is in turn connected to a second automatic gain control (AGC) amplifier 204. The AGC amplifier 204 has a corresponding feedback impedance network 201 comprising a series combination of an inductor 201a and capacitor 201b connected across the amplifier 204. For simplicity the power supply connections of the amplifiers have been omitted.

The AGC amplifier 204 acts to maintain the amplitude of the oscillations provided by the crystal 202a at substantially constant amplitude by automatically adjusting the amount of gain it provides according to the amplitude of the received signal. The first amplifier 203 merely serves to act as a buffer between the output impedance of resonator network 202 and the input impedance of the AGC amplifier 204 and corresponding feedback impedance network. The interposed buffer amplifier 203 prevents the resonator network 202 from loading the AGC amplifier 204 and its corresponding impedance network 201 unacceptably thereby allowing the two parts of the circuit to be connected in series without undesirable loading effects.

The values of the impedance network 201 are chosen to effectively filter the signal around a resonant frequency of the crystal resonator when the crystal is in the environment of interest (e.g. a liquid) thus maintaining oscillations at a desired resonant frequency of the crystal. In particular, the impedance network 201 is designed to ensure the bandwidth of the oscillator 200 is wide enough to accommodate changes in resonant frequency caused by the particular type of event that the oscillator circuit has been configured to detect and hence allow measurement of the biological or other interactions of interest. However, as will be explained in more detail below the impedance network 201 by virtue of having an associated resonant frequency additionally provides the circuit with un-expected bi-stable properties. As will be appreciated although the impedance network 201 is shown as a series combination of an inductor 201a and capacitor 201b other combinations and configurations of reactive and resistive components may be used in order to give a desired frequency response.

Further, in the above embodiment the amplifier 204 is shown as an AGC amplifier, however, the first amplifier 203 could equally be an AGC amplifier and the second amplifier 204 a non-AGC amplifier. This would produce substantially the same result as the configuration illustrated in FIG. 2 and described above.

Figure 3:
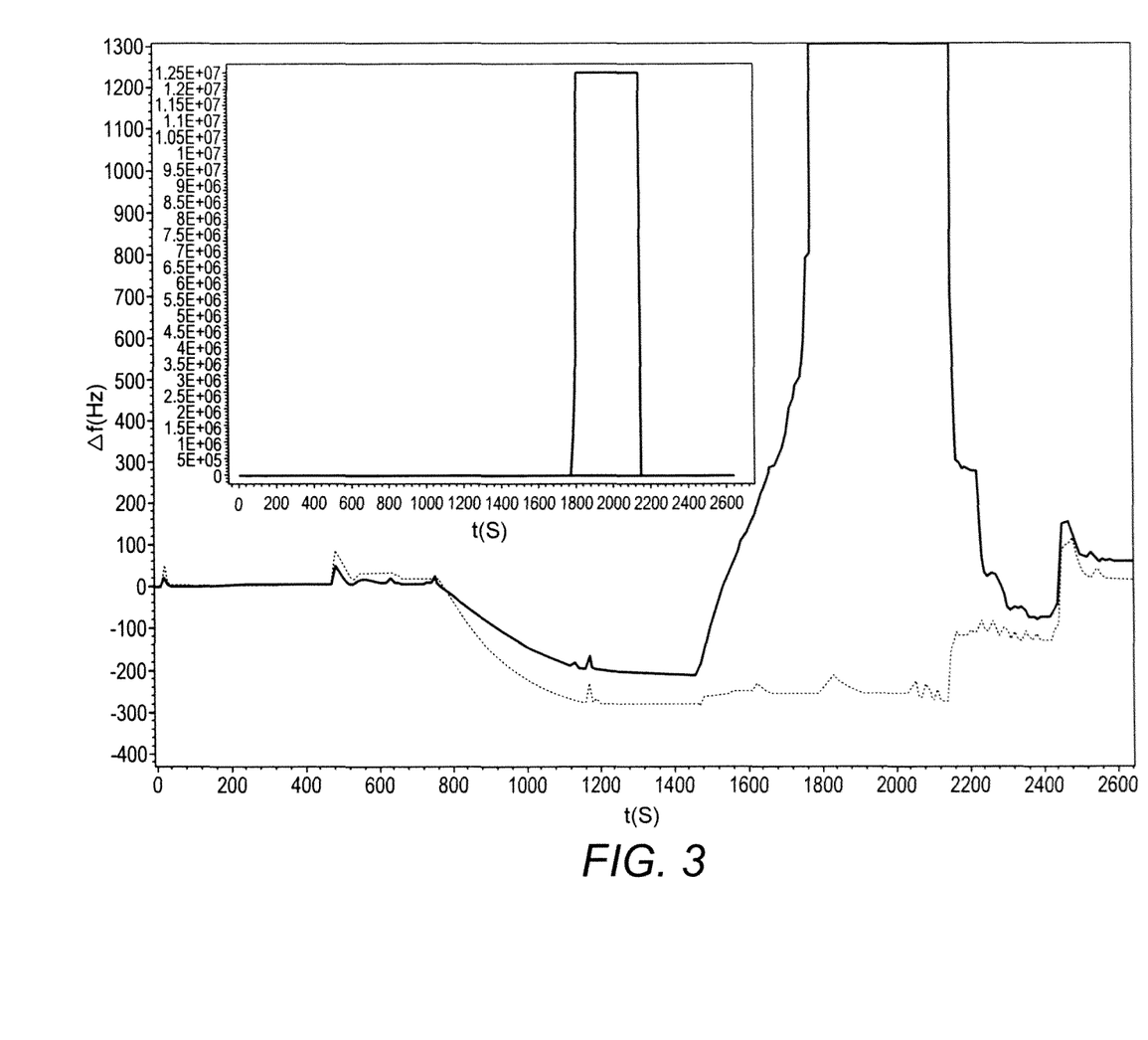
FIG. 3 shows the frequency of the oscillator circuit plotted against time as the sensor becomes loaded and switches to the resonant frequency of the impedance network.

Operation of the oscillator circuit shown in FIG. 2 will now be explained with reference to FIG. 3. FIG. 3 shows a plot of measured frequency against time for the oscillator circuit of FIG. 2 during a binding event where the circuit has the component values Lc=180 nH, L=180 nH, C=150 pF and the crystal 202a has a resonant frequency of 16.5 MHz. The x-axis shows time in seconds and the y-axis show the change in resonant frequency )f. The main plot shows the detail of a control and measurement channel 301 and 302 as beads (paramagnetic particles in this example) start to bind to the surface of the crystal resonator. The inset plot 303 shows the same data but with the scale of the y-axis reduced to show the substantive frequency behaviour of the circuit more clearly.

Beads start to bind to the transducer surface at approximately 800 seconds where the transducer is introduced into the sample to be measured. This causes an initial period from about 800 to 1400 seconds where the resonant frequency of the transducer slowly decreases to a wet equilibrium state as the sensor is introduced to a liquid to be measured. Between 1400 and 1800 seconds the frequency of oscillation increases relatively slowly as beads are adsorbed onto the sensor surface and its resistance increases. At approximately 1800 seconds, however, there is an abrupt change in oscillator frequency.

This can be explained in terms of the behaviour of the oscillator circuit in FIG. 2. Firstly, it is instructive to consider the situation where the crystal is disconnected from the circuit. In such a situation there will effectively be an infinite load connected across the sensor path. The oscillator will still oscillate but at a much higher frequency determined by the resonant properties of the impedance network connected across the AGC amplifier 204 (as this is the only valid path through which current can flow in the circuit). In this particular example this frequency is approximately 29 MHz. However, when a crystal is connected to the circuit the preferred current path is through the crystal. Thus, the frequency of oscillation of the circuit is determined by the resonant properties of the crystal rather than the impedance network. The crystal having a much lower resonant frequency than the impedance network of approximately 16.5 MHz.

As the crystal becomes increasingly loaded, the resistance of the crystal increases correspondingly and the resonant frequency of the crystal (and therefore the oscillation frequency of the oscillator circuit) will gradually change as it would for a conventional QCM. This is the behaviour observed in FIG. 3 from 1400 to 1800 seconds. However, the oscillator circuit of FIG. 2 has the surprising property that when the resistance of the driven crystal part of the circuit 202 increases above a threshold (900 Ohms in this example) the frequency of oscillation will abruptly jump to the resonant frequency of the impedance network. In other words, the circuit starts to behave as it would if no crystal were connected and oscillates around the resonant frequency of the impedance network rather than the resonant frequency of the crystal. Thus, by careful choice of crystal and corresponding components of the impedance network the oscillator circuit 200 can be configured to detect, for example, a desired biological event or interaction. In the example shown in FIG. 3, the load on the sensor increases above 900 Ohms at approximately 1800 seconds at which point the oscillator circuit switches to the resonant frequency of the impedance network.

In the particular example shown in FIG. 3, the crystal load increases beyond 900 Ohms at approximately 1800 seconds at which point the oscillator circuit begins to oscillate through the impedance network 201 and accordingly switches to a frequency of approximately 29 MHz. At approximately 2150 seconds the beads adsorbed to the surface of the sensor are removed by washing and accordingly the oscillator circuit switches abruptly back to the unloaded resonant frequency of the crystal of around 16.5 MHz.

The abrupt and large change in frequency upon reaching the threshold makes any subsequent frequency detection of the oscillator circuit simple. Sophisticated frequency counting or network analysis can be dispensed with and instead, for example, a simple rectifier and integrator circuit can be utilised to provide a measure of whether the frequency is free-running or not. This 'binary' frequency response, therefore, provides a simple and effective measure to detect a desired event using compact and inexpensive circuitry suitable for embedding within a handheld or other portable device.

The shown measurements were made using 0.3 mg/ml of 1.0 μm beads. For a 0.2 ml sample volume this corresponds to $7.1 \times 10^7$ beads per sensor channel. The sensor surface is fully square packed with $1.1 \times 10^6$ beads.

The circuit can be effectively configured by modelling its behaviour utilising an acoustic velocity multi-layer sensor model at the loaded frequency of 16.5 MHz. The analytical techniques and acoustic velocity multi-layer sensor model are described in, for example, "Piezoelectric Sensors", Springer Verlag, Eds. Steinem C., Janshoff A., Springer Series on Chemical Sensors and Biosensors, Vol. 5, 2007, XII, 483 p. 200 illus., ISBN: 978-3-540-36567-9 which is hereby incorporated by reference.

The model predicts a wet resistance load of 725Σ which corresponds to the actual measured value on the 16.5 MHz sensor made utilising a network analyser; the maximum resistance load of the sensor is predicted to be 1900Σ when fully loaded with 1.0 μm beads (78% full square packed) at a shear stiffness of $1 \times 10^5$ Pa; and a total frequency change at maximum packing to be 3 kHz. The data shown in the plot of FIG. 3 shows the oscillation frequency shifting to free running mode after about 1 kHz of frequency change. The model predicts the resistance of the sensor to be approximately (1900−725)/3+725=1100Σ (compared with the 900Σ measured switch point). Thus, the model indicates the switching to the free-running mode is to be expected at around 1100Σ and will occur when the sensor is approximately ⅓ full of 1.0 μm beads.

In the above described circuits the crystal is connected in parallel with inductor $L_c$ which is designed to provide phase compensation for the parasitic capacitance of the crystal. In addition, the inductor will inevitably modify the frequency response and resonant frequency of the crystal. This can be utilised to an advantage if the inductance is chosen to configure the switching point of the circuit to correspond to a particular event. As will be explained below further components can be connected with the resonator crystal either in series or parallel to configure the switching point of the circuit. In a further embodiment the inductor can be omitted altogether without substantially changing the functional performance of the circuit.

Figure 4A:
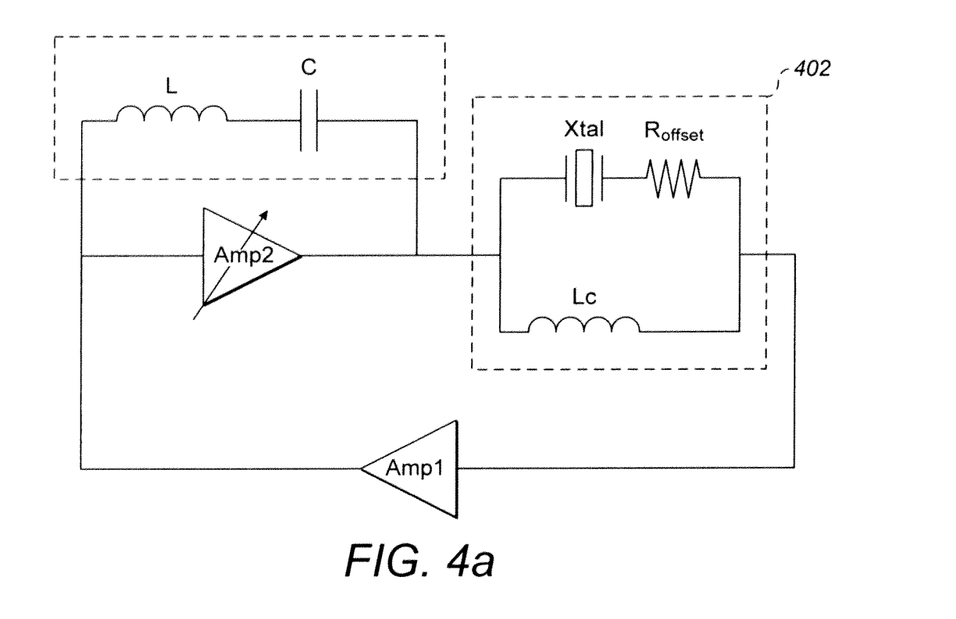
FIG. 4a shows an alternative oscillator circuit in which an offset resistance is connected in series with the crystal resonator.

In the above described embodiment the loading conditions at which the oscillator switches to the resonant frequency of the impedance network are dependent on the properties of the resonator (in this case a quartz crystal oscillator) itself. FIG. 4a shows a further embodiment of an oscillator circuit which substantially corresponds to the circuit of FIG. 2 but wherein the crystal network 402 includes the addition of an offset resistor $R_{offset}$ connected in series with the crystal Xtal.

Figure 4B:
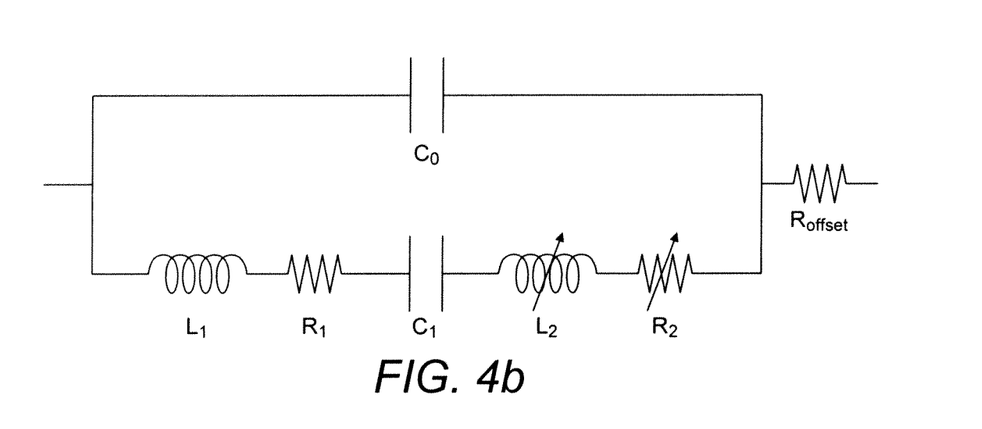

By adding an offset resistance of a predetermined value the switch point can be offset to correspond to a desired event. In effect, changing the offset resistance tunes the switching point of the oscillator circuit to correspond to a predetermined amount of material binding on the sensor. Thus, by tuning the circuit with an offset resistor the circuit can be configured to detect a predetermined biological event. FIG. 4b shows an equivalent circuit corresponding to the crystal with an offset resistor connected in series. $C_0$ is the crystal's equivalent series capacitance and $L_1$, $R_1$ and $C_1$ the equivalent dry inductance, resistance and capacitance respectively. Equivalent circuit components $L_2$ and $R_2$ are a variable inductance and resistance corresponding to the change in impedance caused when material binds to the crystal surface. Offset resistor $R_{offset}$ is a resistive component which as discussed above is connected in series with the crystal sensor to ensure that the variation in $R_2$ due to change in the environment of the crystal or by material binding to the sensor surface causes the total load on the sensor to pass the critical point and cause a change to the free-running frequency.

Figure 5:
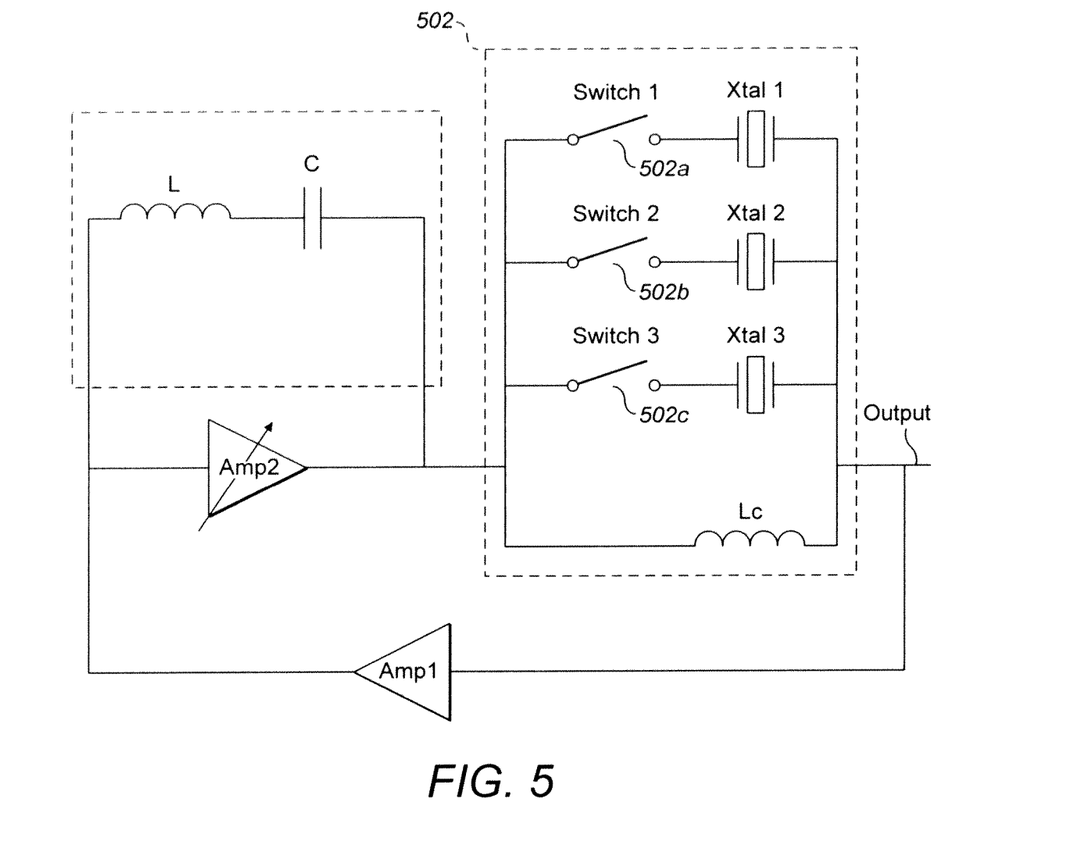
FIG. 5 shows a block diagram of an alternative oscillator circuit comprising multiple crystal resonators with corresponding switches for selecting which resonator forms the sensor in the circuit.

FIG. 5 shows a further embodiment in which the oscillator circuit comprises a plurality of crystals each configured to detect a particular event (e.g. the quantity of material bound to the sensor) and being switch-able in and out of the oscillator circuit.

The oscillator circuit comprises substantially the same components as the oscillator circuit shown in FIG. 2 other than resonator network 502. Resonator network 502 comprises a plurality of crystals $Xtal_1$ to $Xtal_3$ connected in parallel with a single compensation inductor $L_c$. Each crystal has a switch 502a to 502c connected in series with a corresponding crystal Xtal1 to Xtal3, which when closed connects the corresponding crystal to the circuit. When the switch is open, the path containing the corresponding crystal is short circuited and the crystal does not form part of the circuit. Thus, by closing an appropriate switch 502a to 502c a user can select which crystal to utilise as the resonator in the circuit. The circuit can be configured such that it will switch to free-running mode at different switching points depending on which crystal is switched into the circuit. By carefully choosing the geometry and size of the crystals $Xtal_1$ to $Xtal_3$, the switching points can be configured to correspond to predetermined events. For example each crystal could be configured to make the circuit free-run for increasing quantities of material bound to the sensor surface. Therefore, by having a plurality of selectable crystals, the circuit becomes much more versatile and it is possible to detect more than one type of event with a single circuit.

Although, the circuit shown in FIG. 5 comprises three crystals $Xtal_1$ to $Xtal_3$ and three corresponding switches 502a to 502c, it will be appreciated that any number of crystals could be used depending on the application requirements.

Further, it will also be appreciated that corresponding offset resistors (not shown) could be connected in series with each crystal $Xtal_1$ to $Xtal_3$ in order to fine tune the switching point of each crystal $Xtal_1$ to $Xtal_3$.

The switches in the embodiment of FIG. 5 are shown as being manually activated. However, it is also possible to provide external control circuitry to determine the activation of the switches. This concept together with utilising different selectable crystals as the resonator in order to detect different events can be extended by utilising a circuit such as that shown in FIG. 6 whereby each crystal or crystal network is alternately connected to the oscillator circuit utilising a de-multiplexer 605.

Figure 6:
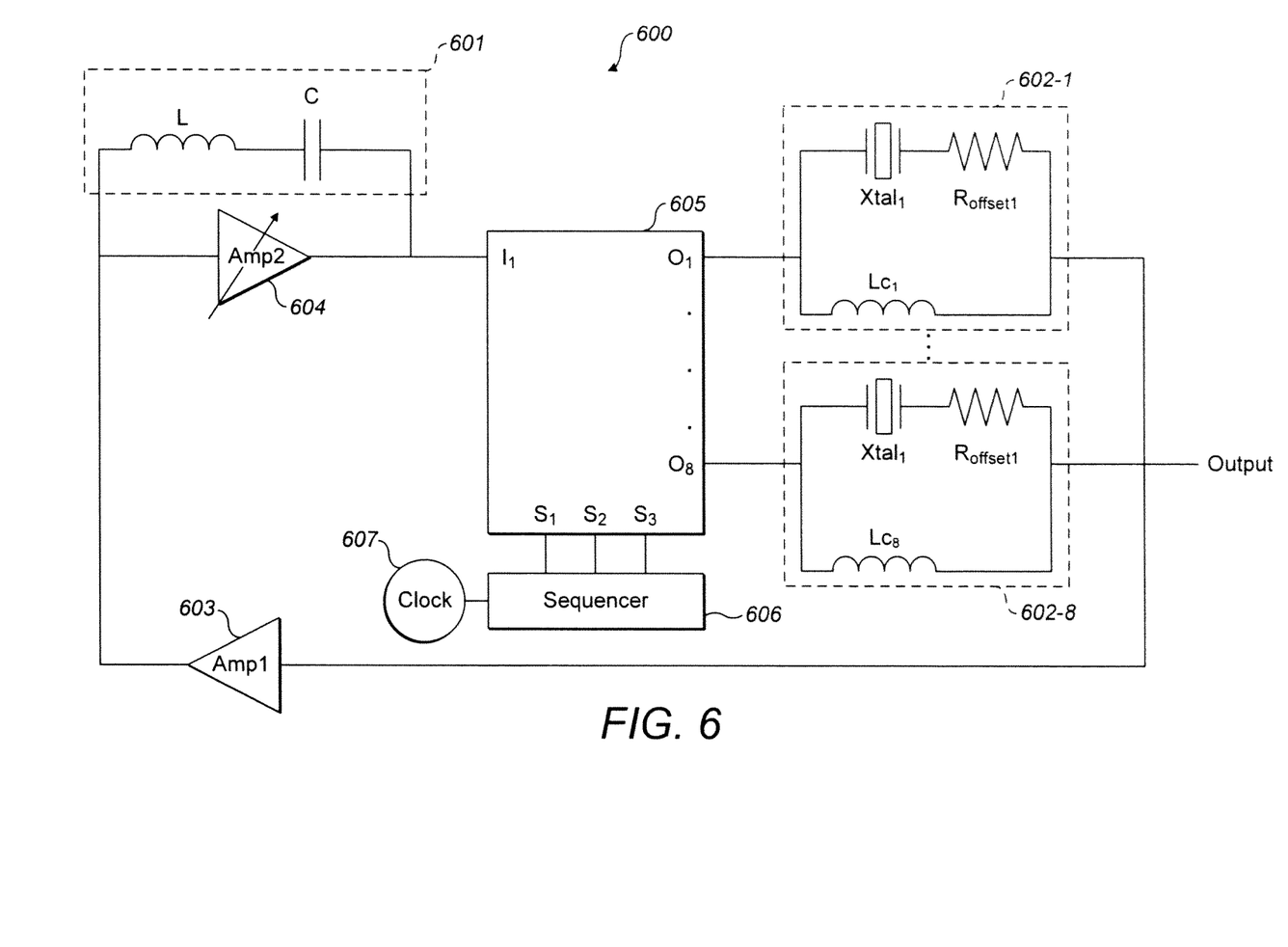
FIG. 6 shows a block diagram of an alternative oscillator circuit comprising a plurality of crystals coupled to a de-multiplexer in which the crystals are alternately switched in and out of the circuit.

As before the oscillator circuit 600 comprises and AGC amp 604 and corresponding impedance network 601 comprising an inductor L, capacitor C and resistor R. However, in this embodiment, the output of the AGC amp 604 is connected to an input of de-multiplexer 605. The de-multiplexer 605 could be a suitable 'off the shelf' commercially available de-multiplexer packaged integrated circuit.

In this embodiment the multiplexer has eight outputs $O_1$ to $O_8$ and has three corresponding selection pins $S_1$ to $S_3$ for selecting the desired output pin. Each output pin $O_1$ to $O_8$ is connected to a corresponding crystal network 602-1 to 602-8. Each crystal network 602-1 to 602-8 comprises a crystal Xtal1 to Xtal8 connected in parallel to a compensation inductor $Lc_1$ to $Lc_8$ in a like manner to the above described oscillator circuits. The crystal networks 602-1 to 602-8 may further comprise an offset resistor $Roffset_1$ to $Roffset_8$ in order that the switching point of the bi-stable oscillator circuit can be fine tuned for each crystal network 602-1 to 602-8. The outputs of each crystal network 602-1 to 602-8 are connected in a feedback loop to the AGC amplifier 604 via the buffer amplifier 603 in the same manner as before.

The circuit 600 further comprises a sequencer 606 which is operable to produce a binary sequence at its output pins. In this embodiment the sequencer has three output pins and is therefore able to produce a pre-programmed sequence utilising the binary equivalent of the decimal numbers one to eight which corresponds to the number of outputs $O_1$ to $O_8$ of the de-multiplexer 605. The sequencer 605 is clocked by means of a clock signal provided by clock 607 and is configured to switch to the next number in the pre-programmed sequence at each rising edge (or alternatively falling edge) of the received clock signal. The output pins of the sequencer are connected to the selection pins $S_1$ to $S_3$ of the de-multiplexer 605. In this way, the outputs of the multiplexer $O_1$ to $O_8$ are alternately switched in accordance with the pre-programmed sequence of the sequencer 606 at regular intervals synchronised with the clock signal.

Thus, each period of the clock signal corresponds to a time window in which a particular crystal network 602-1 to 602-8 will be connected to the oscillator circuit. Thereby it is possible to measure the frequency at each period of the clock pulse to determine whether the detectable event corresponding to the respective crystal network has occurred.

By utilising a similar configuration to the bi-stable oscillator circuit shown in FIG. 6, the principal of using offset resistors to configure the oscillator circuit to detect pre-determined events can be extended by similarly utilising a de-multiplexer this time in combination with a plurality of offset resistors together with a single crystal. An example of such a system is shown in FIG. 7 in which in addition to an oscillator circuit there is additionally provided a de-multiplexer 705, a plurality of offset resistances 708-1 to 708-8 connected to the outputs of the de-multiplexer and a sequencer 706 connected to the select lines of the de-multiplexer.

The multiplexer 705, sequencer 706 and clock 707, which operate in substantially the same manner, are the corresponding components 605, 606 and 607 of the embodiment shown in FIG. 6. Similarly, the amplifiers 703 and 704 together with the impedance network 701 also operate in the same way. However, this embodiment differs from that shown in FIG. 6 in that the branch of the crystal network 702 containing crystal 709 is connected through the multiplexer 705 such that the multiplexer sits between the crystal and the offset resistor. In particular, the crystal 709 in a first branch of the crystal network 702 is connected to input terminal $I_1$ of the multiplexer 705. Offset resistors 708-1 to 708-8 are connected to the outputs $O_1$ to $O_8$ of the multiplexer 705. The branch of the crystal network 702 containing compensation inductor 710 is connected across the multiplexer 705 such that the inductor 710 is connected from the output of the amplifier 704 across the crystal 709, multiplexer 705 and the offset resistors 708-1 to 708-8. This arrangement allows offset resistors 708-1 to 708-8 to be alternately connected to the crystal and oscillator circuit. Thus each offset resistor 708-1 to 708-8 can be chosen to tune the switching point of the oscillator to correspond to a particular event when the resistor is connected to the circuit. This arrangement is advantageous compared to the arrangement shown in FIG. 6 because only a single crystal needs to be used thus making the circuit simpler, compact and cost effective. This reduction in complexity is at the cost of the loss of a degree of design freedom resulting from utilising only a single crystal as a sensor/resonator.

ALTERNATIVE EMBODIMENTS

Figure 7:
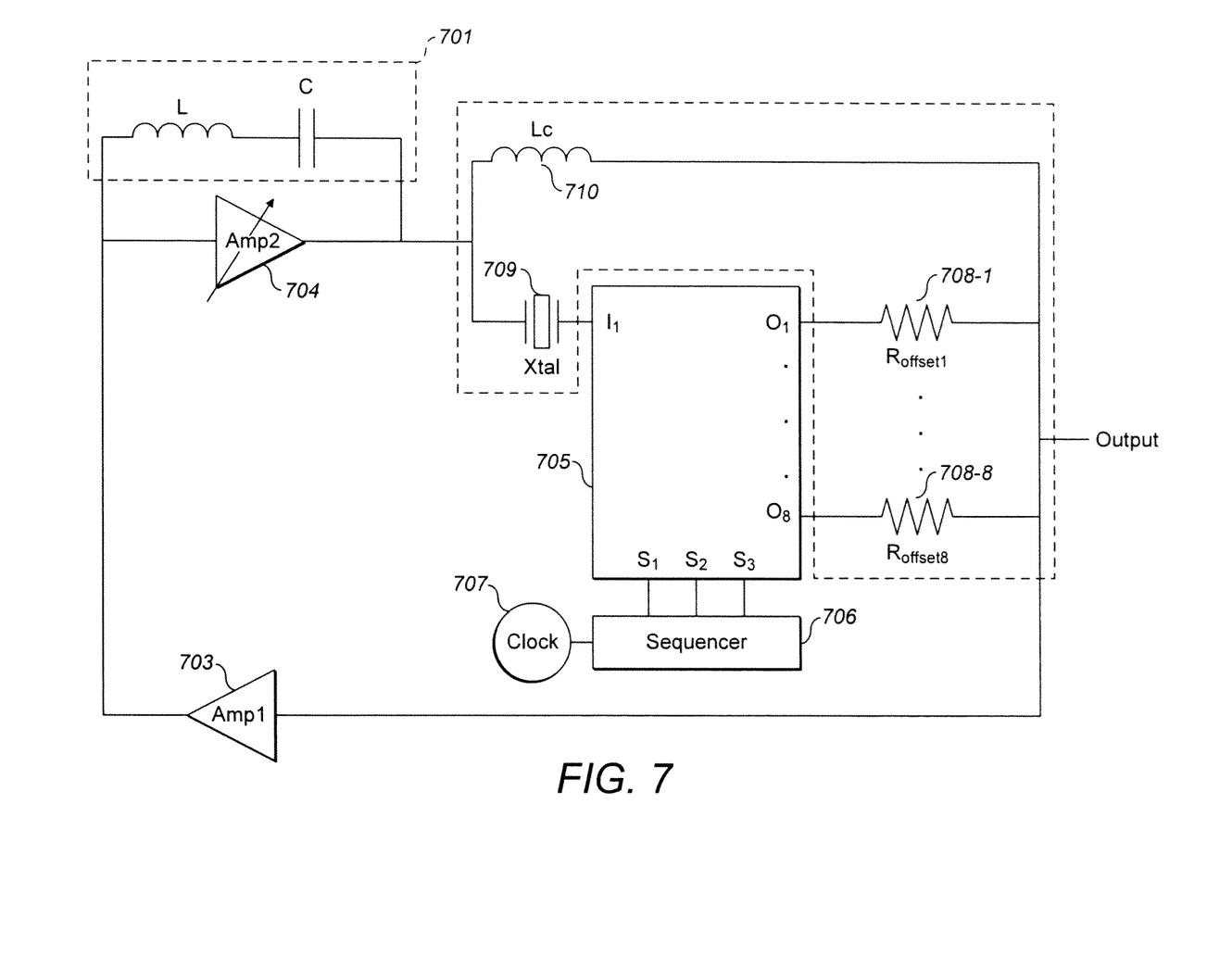
FIG. 7 shows a block diagram of an alternative oscillator circuit comprising a plurality of crystals coupled to a de-multiplexer in which the crystals are alternately switched in and out of the circuit.

In the embodiments shown in FIGS. 6 and 7 and described above the output of the oscillator circuits 600 or 700 is preferably processed by further circuitry (preferably a rectifier and integrator, not shown) to provide a high voltage signal when the oscillator is free running and a low voltage signal when oscillating at the crystal frequency. In a further embodiment, the processed output of the oscillator circuit is connected to a first input of an AND logic gate and the clock signal from the clock 607 or 707 is connected to a second input of the AND gate. The output of the AND gate is connected to the clock input of the sequencer 606. In this way the sequencer (and accordingly the selected output of the de-multiplexer) is switched to the next number in the sequence only when the oscillator circuit with the presently connected crystal network 602-1 to 602-8 has reached its free-running condition. By having each crystal network in the sequence correspond to gradations in the quantity of material bound at the sensor, the output of the sequencer itself can be used to provide a meaningful output signal from the circuit. Each number output by the sequencer corresponding, in this embodiment, to a pre-determined quantity of material having become bound to the sensor. The output signal of the sequencer 606 could be provided to a display or other processing devices in order to provide a useful data output (not shown).

Further, the embodiments shown in FIGS. 6 and 7 show an oscillator circuit in which the de-multiplexer 605 or 705 has 8 outputs selected by a sequencer 606 or 706 having 3 output selection pins. It will be appreciated that further embodiments are possible utilising a de-multiplexer having a different number of output pins and corresponding components depending on the design requirements of the sensor. The output pins provided by the sequencer would be scaled accordingly in order to provide selection across the full range of outputs provided by the de-multiplexer.

In the above embodiments the functional blocks of the oscillator are shown in terms of the individual electronic components that provide the desired functionality. However, in further embodiments any or all of the components forming the impedance network 201, 401, 501, 601 and 701, the amplifiers 203 and 204, 603 and 604, 703 and 704, or the switches 502a to 502c could be provided by single integrated circuit package such as an ASIC or the like.

In the above embodiments, the preferred circuit for obtaining a measure of the frequency of the oscillator circuit has been described in terms of utilising a conventional rectifier, filter and integrator. However, in a further embodiment it is also possible to measure changes in the frequency of the circuit by measuring the gain applied by the AGC amplifier which will have a larger value when the circuit switches abruptly to the resonant frequency of the impedance network. In a yet further embodiment the series resistance of the AGC amplifier is measured by an external detector in order to provide a measure of the frequency change.

In the above described embodiments offset resistances are used to tune or calibrate the oscillator circuit. However, in an alternative embodiment the offset resistance would be replaced by an offset load which could comprise any combination of resistive or reactive components. This has the advantage of improving design freedom in tuning the phase and frequency response of the circuit and the effective switching point of the oscillator.

In the above described embodiments that utilise an offset load, the offset load is provided by a fixed impedance comprising one or more electronic components. In an alternative embodiment the value of the offset load can be adjusted manually. This could be achieved, for example, whereby the offset load comprises a variable resistor that can be adjusted externally by means of a dial or switch. In a further embodiment the impedance could be adjusted automatically by a control circuit (not shown) to change the switching threshold once a switching event has occurred. This is advantageous where for example where it is desirable to detect how a quantity of material binding to the surface increases with time. When a sufficient quantity of material has bound to the surface the frequency will switch, which can be detected by a control circuit. Upon detecting the switching, the control circuit would adjust the offset impedance such that the switching point then corresponded to an increased quantity of material bound to the surface of the resonator.

In one embodiment a plurality of oscillator circuits could be configured to determine the hematocrit of a blood sample. A first circuit might be configured such that it switches at 10% Hct, a second at 25% Hct, a third at 30% Hct, a fourth a 40% Hct, etc. thus by determining for each oscillator circuit whether energy is flowing through the sensor, or not, (by measuring the frequency of oscillation) it will be possible to determine the Hct of the sample.

In a further alternative, instead of using independent circuits a single oscillator circuit such as those shown in FIGS. 5 to 7 and described above could be used. Each offset load and/or resonator being configured to detect a different quantity of Hct.

In another embodiment a sensor may be configured to capture hCG in a urine sample, where a threshold amount indicates pregnancy. When a sensor has reached saturation limit, current will no longer flow through the sensor, but be diverted through the alternate path. Under such instance sample would be considered "positive", i.e. the woman is pregnant.

In a yet further embodiment a series of circuits may be configured to determine the coagulation state of a sample of blood/plasma. The oscillator circuits are configured such that as the viscosity of the blood/plasma sample changes the surface of the resonator in each circuit becomes successively fully loaded such that current is diverted from flowing through the resonator to an alternate path through the circuit.

Sensor devices of the present invention may also find application in drug testing or infectious disease testing where the presence of a threshold amount of substance is sufficient to indicate a positive result.

It is anticipated that the above described bi-stable oscillator will have application in non-biological sensing. For example, with appropriate calibration it could be used to detect a change in density/viscosity of any liquid such as, for example, oil. Further, the sensor is not limited to application of detecting properties of liquids, it is foreseen that a change in the properties of a gas could also be detected provided that the change imparted a detectable load on the surface of the resonator. In fact the bi-stable oscillator circuit can be used to detect any change in the environment to which the surface of the resonator is exposed that imparts a change in load at the resonator surface.

In further exemplary embodiments the circuit is configured to function when the detectable load is placed on the resonator surface includes liquid phase, vapour phase and gaseous phase media. The surface of a resonator may be modified with a "receptor" for the target species of interest present in the sample. When surface sites have been saturated with target species the resonator will become saturated, which will in turn cause the circuit to switch into the free-running condition. In one embodiment the resonator may be modified to respond to a particular biological entity, such as a microbial cell, that may be present in a sample of air. In other embodiments devices might be used to detect the presence of drugs, either in a liquid swab taken from a surface, or in the vapour phase in proximity to a surface containing the drug.

In a further embodiment a resonator may be modified to detect the presence of explosive agents in the vapour phase. In yet further embodiments resonators may be modified to detect contaminants in a liquid sample, wherein when the level of contaminant is below a threshold the level is considered acceptable, but when the level of contaminant exceeds a threshold the oscillator circuit switches frequency. Such an embodiment may include number of microbial organisms in dairy samples, where a certain level of microbes is considered acceptable (safe for human consumption), but above which the product is considered unacceptable. Similarly, in a further embodiment the circuit may be configured to monitor drinking water (in particular bottled water) for unacceptable levels of microbial contamination or for detection of unacceptable levels of toxins potentially present.

The invention claimed is:

1. A bi-stable oscillator circuit for detecting a load imparted to a surface comprising:
    an electrical amplifier;
    at least one resonator comprising an electrical transducer having a resonant frequency, a surface of the resonator forming the surface on which the load is to be detected;
    an impedance network having a resonant frequency;
    wherein the resonator is arranged to be exposed to an environment under test, and the resonator and the impedance network are connected in parallel with the electrical amplifier and the resonator is configured so that a load imparted to the surface causes a change in resonant frequency such that when a load imparted to the surface of the resonator exceeds a pre-determined threshold value the oscillator circuit oscillates at the resonant frequency of the impedance network and when a load imparted to the surface of the resonator is less than the threshold value the oscillator circuit oscillates at the resonant frequency of the resonator, switching of the circuit oscillation frequency being indicative of the load crossing the predetermined threshold value.

2. The bi-stable oscillator circuit according to claim 1 wherein the impedance value of the resonator and impedance network are configured such that the predetermined threshold corresponds to a known event in an environment under test.

3. The bi-stable oscillator circuit according to claim 1 further comprising at least one offset load connected in series or parallel with the resonator wherein the impedance value of the offset load is such that the threshold of the oscillator circuit corresponds to a known event in an environment under test.

4. The bi-stable oscillator circuit according to claim 3 wherein said offset load comprises a resistor, capacitor, inductor or any combination thereof arranged to have an impedance value such that the threshold of the oscillator circuit corresponds to a known event in the environment under test.

5. The bi-stable oscillator circuit according to claim 3 further comprising means to manually adjust the impedance value of the offset load.

6. The bi-stable oscillator circuit according to claim 4 wherein said oscillator circuit further comprises automatic adjustment means operable to automatically change the impedance value of the offset load when the threshold is crossed such that a new threshold is set.

7. The bi-stable oscillator circuit according to claim 1 further comprising frequency detection means operable to detect whether the electrical oscillator circuit is oscillating at the resonant frequency of the resonator or the resonant frequency of the impedance network.

8. The bi-stable oscillator circuit according to claim 7 wherein said frequency detection means comprises a frequency counter.

9. The bi-stable oscillator circuit according to claim 7 wherein said frequency detection means comprises a rectifier and an integrator.

10. The bi-stable oscillator circuit according to claim 1 further comprising:
    a plurality of said at least one resonators;
    a selection circuit connected to the plurality of resonators and operable to sequentially individually connect each of the resonators between an input and the output of the electrical amplifier.

11. The bi-stable oscillator circuit according to claim 10 wherein said selection circuit comprises a de-multiplexer and a sequencer connected to said de-multiplexer wherein:
    the output of the electrical amplifier is connected to a signal input of the de-multiplexer and each resonator is connected to an output of the de-multiplexer; and
    said sequencer is operable to provide a predetermined sequence of signal values to the selection input(s) of the de-multiplexer such that the plurality of resonators are sequentially selected by the de-multiplexer and each resonator is thereby individually connected to the electrical amplifier in the order specified by the predetermined sequence.

12. The bi-stable oscillator circuit according to claim 10 wherein each resonator has an associated offset load connected in series or parallel with the resonator and wherein the impedance value of each offset load is configured such that the threshold at which the oscillator circuit switches to the resonant frequency of the impedance network, when the corresponding resonator is connected via the sequencer, corresponds to a known event in an environment under test.

13. The bi-stable oscillator circuit according to claim 3 wherein said offset load comprises a resistor, capacitor, inductor or any combination thereof configured to provide an impedance value such that the threshold of the oscillator circuit corresponds to the known event in the environment under test.

14. The bi-stable oscillator circuit according to claim 1 further comprising:
a plurality of offset load elements wherein the impedance value of each offset load element is configured to adjust the threshold to correspond to a known event in an environment under test;
a selection circuit operable to sequentially connect each offset load to the resonator in a predetermined sequence.

15. The bi-stable oscillator circuit according to claim 14 wherein said selection circuit comprises a de-multiplexer and a sequencer wherein:
the at least one resonator is connected to an input of the de-multiplexer;
each of the plurality of offset load elements are connected to respective outputs of the de-multiplexer; and
said sequencer is operable to provide a predetermined sequence of signal values to the de-multiplexer such that each offset load element is individually connected to the resonator in the order specified by the sequence.

16. The bi-stable oscillator circuit according to claim 14 wherein any or all of the offset load elements comprise any of a resistor, capacitor, inductor or any combination thereof configured to provide an offset load such that the threshold of the oscillator circuit corresponds to the known event.

17. The bi-stable oscillator circuit according to claim 10 further comprising a clock connected to the sequencer, wherein said sequencer is configured to provide the next signal in the sequence after each clock period.

18. The bi-stable oscillator circuit according to claim 10 wherein the oscillator circuit further comprises a frequency detection circuit operable to generate a first signal output when the oscillator circuit is oscillating at the resonant frequency of the resonator and a second signal output when the oscillator circuit is oscillating at the resonant frequency of the impedance network wherein said second signal is indicative of the load crossing the predetermined threshold value.

19. The bi-stable oscillator circuit according to claim 18 wherein the output of the frequency detection circuit is provided to the sequencer and the sequencer is configured to change to the next signal value in the sequence at each clock period only if the second signal is provided at the output of the frequency detection circuit.

20. The bi-stable oscillator circuit according to claim 18 wherein said frequency detection circuit comprises a rectifier and an integrator or a filter circuit.

21. The bi-stable oscillator circuit according to claim 1 wherein said electrical amplifier comprises an automatic gain controlled (AGC) electrical amplifier.

22. The bi-stable oscillator circuit according to claim 1 wherein the bi-stable oscillator circuit further comprises an electrical buffer amplifier arranged within the circuit such that it substantially isolates the output impedance of the resonator from the input impedance of the electrical amplifier and impedance network.

23. The bi-stable oscillator circuit according to claim 1 wherein said inductive element connected in parallel with the resonator is configured to provide phase compensation for phase shift associated with parasitic capacitance of the resonator.

24. The bi-stable oscillator circuit according to claim 1 wherein the resonator comprises a piezo-electric crystal.

25. The bi-stable oscillator circuit according to claim 1 wherein the resonator comprises an acoustic wave device.

26. The bi-stable oscillator circuit according to claim 25 wherein said acoustic wave device comprises any of a thickness shear mode resonator, bulk acoustic wave transducer, quartz crystal microbalance, flexural-plate-wave-resonator, surface-acoustic-wave resonator, shear-horizontal-acoustic-plate-mode resonator, a MEMS or NEMS device.

27. The bi-stable oscillator circuit according to claim 25 wherein said acoustic wave device is configured to detect the presence of an analyte in a sample of liquid, vapour or gas that is brought into contact with the surface of the at least one resonator.

28. The bi-stable oscillator circuit according to claim 2 wherein the known event in the environment under test is a known biological, chemical or biochemical event.

29. The bi-stable oscillator circuit according to claim 28 wherein the known event is a change in blood coagulation.

30. The bi-stable oscillator circuit according to claim 28 wherein the known event is a change in blood hematocrit.

31. The bi-stable oscillator circuit according to claim 28 wherein the known event is the quantity of hCG in a urine sample.

32. A method of detecting a load imparted to a surface utilising a bi-stable oscillator circuit according to claim 1 comprising:
introducing the resonator to an environment to be monitored;
detecting the frequency of oscillation of the oscillator circuit after the resonator is introduced to the environment; and
determining that the pre-determined load has been imparted to the surface if the frequency of oscillation of the oscillator circuit is substantially equal to the resonant frequency of the impedance network and determining that the pre-determined load has not been imparted to the surface if the frequency of oscillation is substantially equal to the resonant frequency of the resonator.

33. The method of detecting a load imparted to a surface according to claim 32, wherein the environment to be monitored is a liquid phase, vapour phase or gaseous phase sample.

34. The method of detecting a load imparted to a surface according to claim 33, wherein the pre-determined load corresponds to known component of the liquid phase, vapour phase or gaseous phase sample.

35. The method of detecting a load imparted to a surface according to claim 33, wherein the liquid phase is a body fluid sample.

36. The method of detecting a load imparted to a surface according to claim 32 wherein said pre-determined load corresponds to a known biological, chemical or biochemical event.

37. The method of detecting a load imparted to a surface according to claim 36 wherein said event is a change in blood coagulation.

38. The method of detecting a load imparted to a surface according to claim 36 wherein said event is a change in blood hematocrit of a sample.

39. The method of detecting a load imparted to a surface according to claim 36 wherein said event is a change in hCG in a urine sample.

* * * * *